(12) United States Patent
Cotton et al.

(10) Patent No.: US 9,829,481 B2
(45) Date of Patent: Nov. 28, 2017

(54) SENESCENCE TRACERS (71) Applicant: Eberhard Karls Universitaet Tuebingen Medizinische Fakultaet, Tuebingen (DE)

(72) Inventors: Jonathan Cotton, Tuebingen (DE); Bernd Pichler, Scheyern (DE); Kerstin Fuchs, Tuebingen (DE); Anna Teske, Tuebingen (DE); Marcel Krueger, Tuebingen (DE); Christian Kesenheimer, Dusslingen (DE); Klaus Schulze-Osthoff, Tuebingen (DE); Dominic Hildebrand, Tuebingen (DE)

(73) Assignee: EBERHARD KARLS UNIVERSITAET TUEBINGEN MEDIZINISCHE FAKULTAET, Tuebingen (DE)

( * ) Notice: Subject to any disclaimer, the term of this patent is extended or adjusted under 35 U.S.C. 154(b) by 0 days.

(21) Appl. No.: 14/632,475

(22) Filed: Feb. 26, 2015

(65) Prior Publication Data
US 2015/0168374 A1 Jun. 18, 2015

Related U.S. Application Data (63) Continuation of application No. PCT/EP2012/067102, filed on Sep. 3, 2012, which is a continuation of application No. PCT/EP2012/066714, filed on Aug. 28, 2012.

(51) Int. Cl.
| | |
|---|---|
| *C07D 215/42* | (2006.01) |
| *C07D 215/46* | (2006.01) |
| *G01N 33/50* | (2006.01) |
| *G01N 33/58* | (2006.01) |
| *C07H 15/26* | (2006.01) |
| *A61K 49/00* | (2006.01) |

(52) U.S. Cl.
CPC ..... *G01N 33/5005* (2013.01); *A61K 49/0004* (2013.01); *C07D 215/42* (2013.01); *C07D 215/46* (2013.01); *C07H 15/26* (2013.01); *G01N 33/582* (2013.01); *G01N 2800/7042* (2013.01)

(58) Field of Classification Search
CPC ..... A61K 49/00; C07D 215/42; C07D 215/46
See application file for complete search history.

(56) References Cited

U.S. PATENT DOCUMENTS

| 5,773,236 A | 6/1998 | Diwu et al. | |
| 5,795,728 A * | 8/1998 | Dimri | G01N 33/5005 |
| | | | 435/18 |
| 2008/0241856 A1 | 10/2008 | Wong et al. | |
| 2013/0281393 A1* | 10/2013 | Lau | C07H 15/18 |
| | | | 514/32 |

FOREIGN PATENT DOCUMENTS

WO 2014032737 A1 3/2014

OTHER PUBLICATIONS

Alexandrine Maraval et al. Porphyrin-aminoquinoline conjugates as telomerase inhibitors, Org. Biomol. Chem, 2003, 1, 921-927.*
Kirandeep Kaur et al. Quinolines and Structurally related heterocycles as antimalarials, European Jounal of Medicinal Chem, 45, 3245-3264, 2003.*
Maraval, A. et al. "Prophyrin-aminoquinoline conjugates as telomerase inhibitors", Organic & Biomolecular Chemistry, vol. 1 (No. 6), 2003:921-927.
Noppe, G. et al. "Rapid Flow Cytometric Method for Measuring Senescence Associated b-Galactosidase Activity in Human Fibroblasts", Cytometry Part A, vol. 75A (No. 11), 2009:910-916.
Roninson, I. "Tumor Senescence as a determinant of drug response in vivo", Drug Resistance Updates, vol. 5, 2002:204-208.
Chen, K.Y., et al. "A Marked Increase of Fucosylation of Glycoproteins in IMR-90 Human Diploid Fibroblasts During Senescence In Vitro", Biochem. & Biophys. Research Communications, vol. 142 (No. 3), Feb. 1987:767-774.
Kaur, K. et al. "Quinolines and structurally related heterocycles as antimalarials", Euro. J. of Med. Chem., vol. 45 (No. 8), 2010:3245-3264.
Vasquez-Martin, A. et al. "Repositioning chloroquine and metformin to eliminate cancer stem cell traits in pre-malignant lesions", Drug Resistance Updates, vol. 14 (No. 4), 2011:212-213.
PCT Search Report related to Int'l App. No. PCT/EP2012/067102, dated May 28, 2013, (17 pgs.).
European Examination Report for foreign counterpart application EP 12766009.0 (4 pages, dated Jul. 4, 2016).

* cited by examiner

*Primary Examiner* — Michael G Hartley
*Assistant Examiner* — Jagadishwar Samala
(74) *Attorney, Agent, or Firm* — Loeb & Loeb LLP (57) ABSTRACT

The instant invention relates to novel compounds useful for visualizing cell senescence, their preparation and use. In particular, this invention relates to novel fucose and aminoquinoline derivatives useful as senescence traces and their preparation.

6 Claims, 4 Drawing Sheets

Figure 1: FACS Data for nile-red labeled Fucosidase-Inhibitor in HCT116 and MCF7 cells

Figure 2: Light microscope Pictures of ß-Gal-staining Assay in HCT116 and MCF7 cells Figure 3: Lysosome staining of HCT116 and MCF7 with LysoTracker®

Figure 4: FACS Data for dansyl labeled aminoquinoline in HCT116 and MCF7

SENESCENCE TRACERS

CROSS-REFERENCE TO RELATED APPLICATIONS

This application is a continuation of copending international patent application PCT/EP2012/067102 filed on 3 Sep. 2012 and designating the U.S., which has been published in English, and claims priority from international patent application PCT/EP2012/066714. The entire contents of these prior applications are incorporated herein by reference.

FIELD OF THE INVENTION

The instant invention relates to novel compounds useful for visualizing cell senescence, their preparation and use. In particular, this invention relates to novel fucose and aminoquinoline derivatives useful as senescence traces and their preparation.

BACKGROUND OF THE INVENTION

Related Prior Art

Cell senescence is broadly defined as the general biological program by which cellular proliferation is ceased and in which cells enter a cell-cycle arrest. Senescence is thereby accompanied by distinct changes in the cellular metabolism.

Recently senescence is recognised to play an important role in cancer treatment and therapy resistance as well as offer insight into cancer staging and prognosis. Treatment-associated senescence can be a measure of chemotherapeutic success and the detection of senescent cells might also offer diagnostic opportunities for detecting preneoplastic lesions.

One of the most widely used markers for senescent cell is the senescence-associated (SA)-β-galactosidase (β-gal). Several β-gal substrates have been developed and are currently used ex vivo and in vitro to show β-gal expression.

However there still is a need for improved compounds that can act as tracers for cell senescence, in particular it would be useful if such tracers could be used as diagnostic compounds in vivo using non-invasive methods for the visualisation of such tracers.

Recently it has come to light that the α-fucosidase (α-fuc) expression is a more specific indicator of cell senescence. Furthermore it is known that glycosidases such as β-gal and α-fuc are expressed in the lysosomes and that those lysosomes are often notably enlarged in senescent cells.

SUMMARY OF THE INVENTION

The instant inventors have know found that certain fucose and aminoquinoline derivatives carrying fluorescent labels or radiolabels accumulate in senescent cells and can be used to reliably mark and detect senescent cells both in vitro and in viva

An object of the present invention are compounds of formula

A-L-M (I)

in which,
A represents or wherein,
X represents a halo-substituent, and
* represents the binding site to the residue represented by L.
L represents *Y—(CH$_2$)$_n$—# or wherein,
Y is selected from the group consisting of O, N, S, SO and SO$_2$,
n is an integer from 2 to 6,
* represents the binding site to the residue represented by A, and
# represents the binding site to the residue represented by M, and
M represents a fluorophore, a residue comprising at least one atom selected from the group consisting of $^{76}$Br, $^{75}$Br, $^{18}$F, $^{13}$C and $^{11}$C or a combination thereof,
and the salts thereof, the solvates thereof and the solvates of the salts thereof.

Compounds of the invention are the compounds of formulae (I), (Ia), (Ib), (Ic) and (Id) and the salts, solvates and solvates of the salts thereof, as well as the compounds which are encompassed by formula (I), (Ia), (Ib), (Ic) and (Id) and are mentioned hereinafter as exemplary embodiment(s), and the salts, solvates and solvates of the salts thereof, insofar as the compounds encompassed by formula (I), (Ia), (Ib), (Ic) and (Id) and mentioned hereinafter are not already salts, solvates and solvates of the salts.

The compounds of the invention may, depending on their structure, exist in stereoisomeric forms (enantiomers, diastereomers). The invention therefore also encompasses the enantiomers or diastereomers and respective mixtures thereof. The stereoisomerically uniform constituents can be isolated in a known manner from such mixtures of enantiomers and/or diastereomers.

It might be preferred in those compounds of the invention, in which A represents a fucosidyl residue, if this fucosidyl residue is in the natural L-configuration.

If the compounds of the invention may occur in tautomeric forms, the present invention encompasses all tautomeric forms.

Salts preferred for the purposes of the present invention are physiologically acceptable salts of the compounds of the invention. Also encompassed however are salts which are themselves not suitable for pharmaceutical applications but can be used for example for the isolation or purification of the compounds of the invention.

Examples of pharmaceutically acceptable salts of the compounds of formula (I) include salts of inorganic bases like ammonium salts, alkali metal salts, in particular sodium or potassium salts, alkaline earth metal salts, in particular magnesium or calcium salts; salts of organic bases, in particular salts derived from cyclohexylamine, benzylamine, octylamine, ethanolamine, diethanolamine, diethylamine, triethylamine, ethylenediamine, procaine, morpholine, pyrroline, piperidine, N-ethylpiperidine, N-methylmorpholine, piperazine as the organic base; or salts with basic amino acids, in particular lysine, arginine, ornithine and histidine.

Examples of pharmaceutically acceptable salts of the compounds of formula (I) also include salts of inorganic acids like hydrochlorides, hydrobromides, sulfates, phosphates or phosphonates; salts of organic acids, in particular acetates, formates, propionates, lactates, citrates, fumarates, maleates, benzoates, tartrates, malates, methanesulfonates, ethanesulfonates, toluenesulfonates or benzenesulfonates; or salts with acidic amino acids, in particular aspartate or glutamate.

Solvates for the purposes of the invention refer to those forms of the compounds of the invention which in the solid or liquid state form a complex by coordination with solvent molecules. Hydrates are a specific form of solvates in which the coordination takes place with water.

In the context of this invention the substituents have the following definitions unless specified otherwise.

The term alkyl generally refers to branched or straight-chain $(C_1-C_6)$-alkyl, preferably $(C_1-C_4)$-alkyl, such as in particular methyl, ethyl, propyl, butyl, isopropyl, isobutyl and tert.-butyl.

The term alkoxy generally refers to branched or straight-chain $(C_1-C_6)$-alkoxy, preferably $(C_1-C_4)$-alkoxy, such as in particular methoxy, ethoxy, propoxy, butoxy, isopropoxy, isobutoxy and tert.-butoxy.

The terms mono- and dialkylamino respectively represent an alkylamino radical having one or two alkyl substituents (chosen independently of one another), by way of example and preferably methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-tert-butyl-N-methylamino, N-ethyl-N-n-pentylamino and N-n-hexyl-N-methylamino. Mono-$(C_1-C_3)$-alkylamino represents for example a monoalkylamino radical having 1 to 3 carbon atoms. Di-$(C_1-C_3)$-alkylamino represents a dialkylamino radical having 1 to 3 carbon atoms each per alkyl substituent.

The term halogen or halo refers to fluorine, chlorine, bromine or iodine; preferably fluorine, chlorine or bromine. In some embodiments the term halogen or halo preferably refers to $^{76}Br$, $^{75}Br$, $^{19}F$ and $^{18}F$.

In formulae of the group which are represented by A, the end point of the line adjacent to which there is an *, is not a carbon atom or a $CH_2$ group but rather a component of the bond to the atom to which A is attached.

In the formulae of the group which are represented by L, the end point of the line adjacent to which there is an * or #, is not a carbon atom or a $CH_2$ group but rather a component of the bond to the atom to which L is attached.

The residue represented by M in the compounds of the invention can in its broadest form be any fluorophore known to a person skilled in the art that can be attached to the residue represented by L in the compounds of the invention. Preferably the fluorophore is substantially non-toxic within the concentration range at which the compounds of the invention are used.

The residue represented by M in the compounds of the invention in its broadest form can also be any residue that comprises at least one atom selected from the group consisting of $^{76}Br$, $^{75}Br$, $^{18}F$, $^{13}C$ and $^{11}C$ that can be attached to the residue represented by L in the compounds of the invention. Preferably the residue that comprises at least one atom selected from the group consisting of $^{76}Br$, $^{75}Br$, $^{18}F$, $^{13}C$ and $^{11}C$ is substantially non-toxic within the concentration range at which the compounds of the invention are used. In one of its simplest forms M can be a $^{76}Br$, $^{75}Br$ or $^{18}F$ atom or a $^{13}CH_3-$ or $^{11}CH_3$-group.

A combination of a fluorophore and a residue that comprises at least one atom selected from the group consisting of $^{76}Br$, $^{75}Br$, $^{18}F$, $^{13}C$ and $^{11}C$ can be either a fluorophore that comprises at least one atom selected from the group consisting of $^{76}Br$, $^{75}Br$, $^{18}F$, $^{13}C$ and $^{11}C$ or a residue that comprises both a fluorophore and a second residue that comprises at least one atom selected from the group consisting of $^{76}Br$, $^{75}Br$, $^{18}F$, $^{13}C$ and $^{11}C$.

The present invention also relates to compounds of formula (I) in which X represents Cl.

The present invention also relates to compounds of formula (I) in which n is 2, 3 or 4.

The present invention also relates to compounds of formula (I) in which M represents a fluorophore, preferably a fluorophore selected from the group consisting of, the xanthene derivatives, in particular fluorescein, rhodamine, Oregon green, eosin, and Texas red, the cyanine derivatives, in particular cyanine, indocarbocyanine, oxacarbocyanine, thiacarbocyanine, and merocyanine, the naphthalene derivatives, in particular a dansyl or derivatives thereof, the coumarin derivatives, the oxadiazole derivatives, in particular pyridyloxazole, nitrobenzoxadiazole and benzoxadiazole, the pyrene derivatives, the oxazine derivatives, in particular Nile red, Nile blue and cresyl violet, the acridine derivatives, in particular proflavin, acridine orange and acridine yellow, the arylmethine derivatives, in particular auramine, crystal violet and malachite green, and the tetrapyrrole derivatives, in particular porphin, phthalocyanine and bilirubin.

The present invention also relates to compounds of formula (I) in which M is selected from $^{76}Br$, $^{75}Br$, $^{18}F$, wherein, X is selected from the group consisting of Br, $^{76}Br$, $^{75}Br$, Cl, F and $^{18}F$, $R_1$ represents hydrogen or $(C_1-C_6)$-alkyl,
  whereby alkyl may be substituted with one to three substituents selected independently form the group consisting of, hydroxy, amino, cyano, nitro, halogen, carbonyl, $(C_1-C_4)$-alkoxy, mono $(C_1-C_4)$-alkylamino and di-$(C_1-C_4)$-alkylamino,
  whereby $R_1$ represents an optionally substituted $(C_1-C_6)$-alkyl comprising at least one $^{76}Br$, $^{75}Br$, $^{18}F$ or $^{11}C$ if X is not $^{76}Br$, $^{75}Br$ or $^{18}F$, $R_2$ and $R_3$ independently from one another represent hydrogen or $(C_1-C_6)$-alkyl,
  whereby alkyl may be substituted with one to three substituents selected independently form the group consisting of, hydroxy, amino, cyano, nitro, halogen, carbonyl, $(C_1-C_4)$-alkoxy, mono $(C_1-C_4)$-alkylamino and di-$(C_1-C_4)$-alkylamino, whereby at least on of $R_2$ and $R_3$ represents a $(C_1-C_6)$-alkyl comprising at least one $^{11}C$ or being substituted with a residue comprising at least one $^{76}Br$, $^{75}Br$, $^{18}F$ or $^{11}C$, and \* represents the binding site to the residue represented by L.

In some embodiments it may be preferred if M represents wherein,

X is selected from the group consisting of Br, $^{76}Br$, $^{75}Br$, Cl, F and $^{18}F$, $R_1$ represents hydrogen or $(C_1-C_6)$-alkyl, whereby alkyl may be substituted with one to three substituents selected independently form the group consisting of, hydroxy, amino, cyano, nitro, halogen, carbonyl, $(C_1-C_4)$-alkoxy, mono $(C_1-C_4)$-alkylamino and di-$(C_1-C_4)$-alkylamino, whereby $R_1$ represents an optionally substituted $(C_1-C_6)$-alkyl comprising at least one $^{76}Br$, $^{75}Br$, $^{18}F$ or $^{11}C$ if X is not $^{76}Br$, $^{75}Br$ or $^{18}F$, and \* represents the binding site to the residue represented by L.

In some embodiments it may be preferred if A represents wherein X is as defined above, preferably chlorine.

In some embodiments it may be preferred if A represents preferably

In some embodiments it may be preferred if the compound of formula (I) is a compound of formula (Ia)

wherein $R_1$, L and X have the meaning indicated above, preferably (Ib)

wherein $R_1$, L and X have the meaning indicated above.

In some embodiments it may be preferred if the compound of formula (I) is a compound of formula (Ic)

wherein $R_1$, Y, X and n have the meaning indicated above and Y preferably represents O or N, preferably (Id)

wherein $R_1$, Y, X and n have the meaning indicated above and Y preferably represents O or N, The compounds of the invention can be prepared by various route depending on the precise nature of A, L and M.

It is for example possible to start from a protected fucose and convert the protected fucose to a protected 2-bromo-fucose derivative.

This reaction generally takes place in the presence of a brominating reagent, optionally in a solvent, at a temperature from 0° C. to the reflux of the solvent.

Suitable brominating agents include $PBr_3$ and HBr in acetic acid.

Preferred solvents are halogenated hydrocarbons such as dichloromethane or trichloromethane.

The 2-bromofucose derivative can in the next step be reacted with a compound that will form the residue represented by L in the compounds of the invention.

Examples for such compounds include ethylene glycol, 2-amino-ethanol, 1,2-ethylenediamine, 1,3-propanediol, 3-amino-1-propanol and 1,3-diaminopropane.

The conditions for such a coupling reaction are well known to a person skilled in the art.

The A-L-conjugate obtained this way can then again be coupled under conditions know to a person skilled in the art to a compound corresponding to the residue represented by M in the compounds of the invention.

After the final coupling step any protecting group present in the obtained compound is removed to obtain the compounds of the invention.

It is also possible to convert the 2-bromofucose derivative into the corresponding azide and react this azide with a suitable alkyne using conditions usual for a click reaction followed by further coupling steps and (a) deprotection reaction(s) where appropriate. In this case compounds will be obtained in which L represents a triazole.

Another route to the compounds of the invention involves reacting a compound corresponding to the residue represented by M in the compounds of the invention with a compound that will form the residue represented by L in the compounds of the invention. The M-L-conjugate can then again be coupled to a compound corresponding to the residue represented by A in the compounds of the invention followed (a) deprotection reaction(s) where appropriate.

Some exemplary, non-limiting synthetic routes for the compounds of the invention are displayed in the following schemes. The reactions of reaction scheme 1 result in a protected intermediate that can be deprotected e.g. via a method in analogy to the final step shown in reaction scheme 2 to give the compounds of the invention.

Reaction scheme 1:

Reaction scheme 2:

→

11CH₃I, NaOH, DMF

The compounds of the invention show a valuable range of pharmacological effects which could not have been predicted. They are capable of marking senescent cells.

The invention therefore further relates to the use of the compound of the invention in a method of detecting cell senescence.

The invention therefore further relates to the use of the compound of the invention a method of determining the efficiency of cancer treatment.

The invention therefore further relates to a medicament comprising a compound according to the invention in combination with at least one inert, non-toxic, pharmaceutically suitable excipient.

The invention therefore further relates to the use of the compound of the invention for detecting cell senescence.

The invention therefore further relates to the use of the compound of the invention for determining the efficiency of cancer treatment.

Method for detecting cell senescence comprising contacting cells with a compound of the invention.

Method for determining the efficiency of cancer treatment comprising contacting cells with a compound of the invention.

The above methods can be performed both in vivo, e.g. in a human patient to monitor the efficiency of cancer treatment or in vitro, e.g. to screen for new medicaments.

The compounds will preferably be administered parenterally.

For this administration route the compounds of the invention can be administered in suitable administration forms.

Parenteral administration can take place with avoidance of an absorption step (e.g. intravenous, intraarterial, intracardiac, intraspinal or intralumbar) or with inclusion of an absorption step (e.g. intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

The compounds of the invention can be converted into the stated administration forms. This can take place in a manner known per se by mixing with inert, non-toxic, pharmaceutically acceptable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulfate, polyoxysorbitan oleate), binders (for example polyvinylpyrrolidone), synthetic and natural polymers (for example albumin), stabilizers (e.g. antioxidants such as, for example, ascorbic acid), colors (e.g. inorganic pigments such as, for example, iron oxides) and taste and/or odor corrigents.

The percentage data in the following tests and examples are, unless indicated otherwise, percentages by weight; parts are parts by weight. Solvent ratios, dilution ratios and concentration data of liquid/liquid solutions are based in each case on volume. The statement "w/v" means "weight/volume". Thus, for example, "10% w/v" means: 100 ml of solution or suspension contain 10 g of substance.

BRIEF DESCRIPTION OF THE DRAWINGS

FIG. 4: FACS-analysis data for the compound of Example 2 in HCT116 and

MCF7 cells with (senescence +) and without 250 nM Doxorubicin treatment. The cells were incubated 20 min in 37° C. with 5% CO2. Cells were labeled with 40 ng/ml of the compound of Example 2.Both HCT116 and MCF7 cells treated with Doxorubicin showed enhanced enrichment of the labeled molecule without the need for permiablization.

DESCRIPTION OF PREFERRED EMBODIMENTS

General Methods

All LCMS data (unless otherwise specified) was obtained using an Agilent ESI/APCI HPLC-ms system with a Phenomenex (Luna C-18, 250×4.60 mm, 5 micron) column. The samples were run using a gradient of 5% CH₃CN in water (+0.1% AcOH) for 2 minutes and then increased to 100% CH₃CN over 26 minutes, after which the solvent was maintained at 100% CH₃CN for a further 2 minutes.

Starting Materials and Intermediates

EXAMPLE 1A

N¹-(7-chloroquinolin-4-yl)ethane-1,2-diamine

A solution of 4,7-dichloroquinoline (5.0 g, 25.2 mmol) in ethylenediamine (15 g, 250 mmol) was heated to 90° C., stirring overnight under Argon. TLC indicated the complete consumption of the starting quinoline, with a spot-to-spot conversion into a more polar product. 6M NaOH (30 mL) was added and the organic material was extracted into DCM (3×100 mL). After washing with brine (2×100 mL), drying over MgSO$_4$, the solvents were removed under vacuum, yielding 2.0 g of a colourless crystalline solid, which was not purified further. The identity and purity were confirmed using LCMS, revealing a single uv active peak (3.47 minutes, m/z 221.7 [M]$^+$).

EXAMPLE 2A (3S,4R,5R,6S)-6-methyltetrahydro-2H-pyran-2,3,4,5-tetrayl tetraacetate To a boiling solution of acetic anhydride (35 mL) and NaOAc (2.5 g, 30.5 mmol) was added L-fucose (5 g, 30.5 mmol) in small portions. Once the solution became translucent, it was removed from the heat and partially solidified upon cooling. The residues were poured over crushed ice (50 g) and solid sodium bicarbonate was added until the evolution of gas ceased. The organic material was extracted into EtOAc (3×100 mL), washed with sodium bicarbonate (100 mL) and brine (100 mL) and dried over MgSO$_4$. Removing the solvents under vacuum, resulted in a yellow syrup (10.1 g, 99.6%).

EXAMPLE 3A (3S,4R,5R,6S)-6-methyltetrahydro-2H-pyran-2,3,4,5-tetrayl tetrabenzoate L-fucose (2.0 g, 12.2 mmol) was dissolved in pyridine (15 mL) and cooled to 0° C. in an ice bath. Benzoyl chloride (7.1 mL, 60.1 mmol) was added though a dropping funnel over 5 minutes, after which the ice bath was removed and the reaction was allowed to stir at RT for 3 hours. The reaction mixture was poured into ice-water (100 mL) and extracted into EtOAc (3×100 mL). The residues were washed with ice-cold 1 M HCl (2×100 mL) and brine (100 mL), followed by drying over MgSO$_4$. After removal of solvents under vacuum, the resulting semi-solid was purified using silica-gel column chromatography (EtOAC:PE=3:7), yielding a crystalline colourless solid (6.9 g, 93%).

EXAMPLE 4A (2R,3S,4R,5R,6S)-2-bromo-6-methyltetrahydro-2H-pyran-3,4,5-triyl triacetate To a solution of HBr (10 mL, 33% in AcOH) was added the compound of Example 2A (2.1 g, 6.3 mmol). The reaction was allowed to stir for 2 hours at RT, after which it was poured over crushed ice (50 g). After extraction into DCM (3×30 mL), the combined organic phases were washed repetitively with portions of sodium bicarbonate (3 to 7×50 ml) until neutral. Drying over MgSO$_4$ and removal of solvents under vacuum, afforded the bromide as a thick orange syrup. Due to its instability, it was not purified further but used directly in the following reactions.

EXAMPLE 5A (2R,3S,4R,5R,6S)-2-bromo-6-methyltetrahydro-2H-pyran-3,4,5-triyl tribenzoate The compound of Example 3A (1.1 g, 1.9 mmol) in dry DCM (6 mL) was cooled to 0° C. in a RBF fitted with a rubber septum. After degassing and charging the vessel with Argon, PBr$_3$ (0.285 mL, 3.1 mmol), followed by water (0.190 mL, 10.5 mmol) were added dropwise through separate disposable syringes. After 15 minutes of stirring at 0° C., the ice bath was removed and the reaction was allowed to stir at RT for 3 hours. DCM (50 mL) was added, followed by water (50 mL). The residues were further extracted into DCM (2×30 mL), washed with sodium bicarbonate (2×50 mL), brine (50 mL) and dried over MgSO$_4$. After the solvent was removed under vacuum, the resulting colourless solid, shown pure by TLC, remained (1.0 g, 98%).

EXAMPLE 6A (2S,3S,4R,5R,6S)-2-(2-hydroxyethoxy)-6-methyltetrahydro-2H-pyran-3,4,5-triyl triacetate The compound of Example 4A (4.0 g, 11.3 mmol), ethylene glycol (7.0 g, 112.7 mmol) and Ag₂CO₃ (4.7 g, 16.9 mmol) in dry CH₃CN (25 mL) were stirred for 24 hours at RT under a calcium chloride drying tube. The solution was filtered through a pad of celite to remove all of the solid material, after which sodium bicarbonate (150 mL) was added and the organic material extracted into DCM (3×100 mL). After drying over MgSO₄ and removing the solvents under vacuum, the resulting orange oil was purified using silica-gel column chromatography (EtOAC:PE=2:5), affording the title compound as an orange oil (1.5 g, 40%).

EXAMPLE 7A (2S,3R,4R,5S,6S)-2-methyl-6-(2-(tosyloxy)ethoxy)tetrahydro-2H-pyran-3,4,5-triyl triacetate Tosyl chloride (1.1 g, 3.0 mmol) was added to a solution of the compound of Example 6A (1.0 g, 3.0 mmol) and pyridine (1 mL) in DCM (15 mL), stirring at 0° C. for 30 minutes. The reaction was then allowed to warm to RT and stirred overnight, after which sodium bicarbonate (50 mL) was added and the organic material extracted into DCM (3×50 mL). After washing with brine (2×30 mL) and aqueous 10% copper sulphate, the crude product was dried over MgSO₄, concentrated under vacuum and was purified using silica-gel column chromatography (EtOAC:PE=2:5) to afford the title compound as a crystalline white solid (0.43 g, 29%).

EXAMPLE 8A 2-((7-chloroquinolin-4-yl)amino)ethanol 4,7-dichloroquinoline (11.6 g, 58.6 mmol) in 2-aminoethanol (45 mL, 1.37 mol) was refluxed under Argon overnight. After cooling to RT, 1M NaOH (100 mL) was added and allowed to stir for 10 minutes. The resulting yellow solid material was collected using a Büchner funnel, washed with water (5×100 mL) and dried thoroughly under vacuum, affording the title compound as a light yellow solid (12.27 g, 94%).

EXAMPLE 9A (3S,4R,5R,6S)-2-(2-((7-chloroquinolin-4-yl)amino)ethoxy)-6-methyltetrahydro-2H-pyran-3,4,5-triyl triacetate A solution containing the compound of Example 2A (2.0 g, 6.0 mmol), the compound of Example 8A (2.0 g, 9.0 mmol) and mol-sieve 4 Å (5 g) in dry DCM (15 mL) was prepared, degassed and allowed to stir under argon for 10 minutes at 0° C. in an ice bath. BF₃.OEt₂ (2.6 g, 18.2 mmol) was added through a rubber septum and the reaction was maintained at 0° C. for a further 30 minutes, after which the ice bath was removed and the reaction was allowed to stir at RT overnight. The next day, the reaction mixture was filtered through a pad of celite and washed thoroughly with DCM (3×20 mL). The organic residue was washed until neutral with sodium bicarbonate (3×50 mL), after which it was further washed with brine (50 mL), dried over MgSO₄ and the solvent removed under vacuum. The crude mixture was purified using silica gel column chromatography (MeOH:EtOAc:NEt3=10:90:1), which afforded the title compound as a yellow semi-solid (0.6 g, 20%). The identity was confirmed by LCMS (10.58 minutes, m/z 494.6 [M]⁺).

EXAMPLE 10A (3S,4R,5R,6S)-2-(2-((7-chloroquinolin-4-yl)amino)ethoxy)-6-methyltetrahydro-2H-pyran-3,4,5-triyl tribenzoate A solution containing the compound of Example 3A (3.3 g, 5.7 mmol), the compound of Example 8A (1.9 g, 8.3 mmol) and mol-sieve 4 Å (10 g) in dry DCM (30 mL) was prepared, degassed and allowed to stir under argon for 10 minutes at 0° C. in an ice bath. BF3.OEt₂ (4.8 g, 35.06 mmol) was added through a rubber septum and the reaction was maintained at 0° C. for a further 30 minutes, after which the ice bath was removed and the reaction was allowed to stir at RT overnight. The next day, the reaction mixture was filtered through a pad of celite and washed thoroughly with DCM (3×30 mL). The organic residue was washed until neutral with sodium bicarbonate (3×50 mL), after which it was further washed with brine (50 mL), dried over MgSO₄ and the solvent removed under vacuum. The crude mixture was purified using silica gel column chromatography (MeOH:EtOAc:NEt3=10:90:1), which afforded the title compound as a yellow semi-solid (0.9 g, 23%). The identity was confirmed by LCMS (13.29 minutes, m/z 680.6 [M]⁺).

EXAMPLE 11A (3S,4R,5R,6S)-2-(2-((7-chloroquinolin-4-yl)(methyl)amino)ethoxy)-6-methyltetrahydro-2H-pyran-3,4,5-triyl tribenzoate To a solution of the compound of Example 11A (107 mg, 0.17 mmol) and $K_2OC_3$ (40 mg, 0.29 mmol) in DMF (5 mL), stirring at RT under argon, was added $CH_3I$ (50 mg, 0.35 mmol). The reaction was heated to 90° C. for 1 hour. The reaction mixture was poured into a saturated solution sodium bicarbonate (50 mL), extracted into DCM (3×50 mL) and washed with brine (50 mL). Drying over $MgSO_4$ and removing the solvent under vacuum, afforded the intermediate as an yellow oil. No purification was attempted and the crude reaction mixture was carried over the next step. The identity was confirmed by LCMS (13.64 minutes, m/z 695.7 $[M]^+$).

EXAMPLE 12A 2-((7-chloroquinolin-4-yl)amino)ethyl 4-methylbenzenesulfonate A solution of the compound of Example 8A (1.0 g, 4.5 mmol) and pyridine (1 mL, 12.4 mmol) in DCM (13 mL) was prepared and cooled with stirring in an ice-bath. Tosyl chloride (0.9 g, 4.7 mmol) was added and the reaction was allowed to warm to RT. Saturated aqueous sodium bicarbonate (100 mL) was added and the organics extracted into DCM (3×50 mL), followed by washings with more sodium bicarbonate (2×50 mL) and brine (50 mL). The organic material was dried over $MgSO_4$, the solvents removed under vacuum and purified using silica gel column chromatography (MeOH:EtOAc:$NEt_3$=5:95:1-MeOH:EtOAc:$NEt_3$=10:90:1), affording the title compound as a yellow solid (0.55 g, 33%).

EXAMPLE 13A 4-(diethylamino)-2-nitrosophenol

A solution containing 3-diethylaminophenol (15.0 g, 90.7 mmol) in concentrated HCl (100 mL) was prepared and cooled to 0° C. in an ice-bath. $NaNO_2$ (6.9 g, 100.0 mmol) in water (50 mL) was added slowly over 40 minutes such that no brown $NO_x$ vapours were observed. The reaction was left to stir for 2 hours, after which the thick precipitate was filtered using a Büchner funnel and washed with small portions of water (3×50 mL). After drying the solid for 1 hour on the Büchner funnel, the solid material was dissolved into EtOH (70 mL), $Et_2O$ (35 mL) was added and the solution stored at −20° C. overnight to allow for crystallization. The next day, the solid material was collected by vacuum filtration, using a Büchner funnel and air dried. The product was an orange/red solid (8.8 g, 50%).

EXAMPLE 14A 9-(diethylamino)-2-hydroxy-5H-benzo[a]phenoxazin-5-one

The compound of Example 13A (7.0 g, 36.0 mmol) and 1,6-dihydroxynaphthelene (5.9 g, 36.1 mmol) were refluxed in DMF (100 mL) for 3 hours. After the solvents were removed under vacuum, the residue was redissolved in methanol and adsorbed onto silica and purified using silica gel column chromatography (MeOH:$NEt_3$=50:1) to afford the title compound as a dark purple solid (11.1 g, 92%).

EXAMPLE 15A 2-(bromomethoxy)-9-(diethylamino)-5H-benzo[a]phenoxazin-5-one A solution containing the compound of Example 14A (4.2 g, 12.6 mmol), $K_2CO_3$ (2.5 g, 18.1 mmol) and 1,3-dibromopropane (25.2 g, 126 mmol) in DMF (30 mL) was refluxed for 2 hours. The solvent was removed under vacuum and the crude solid purified using silica gel column chromatography (EtOAc:Pet Ether:$NEt_3$=40:60:1), affording the title compound as a purple solid (1.1 g, 19%). LCMS confirmed the product with a uv-peak (21.40 minutes, m/z 454.6 $[M+H]^+$).

EXAMPLE 16A (2R,3S,4R,5R,6S)-2-mercapto-
6-methyltetrahydro-
2H-pyran-3,4,5-triyl triacetate

The compound of Example 4A (1.5 g, 4.3 mmol) and thiourea (0.4 g, 5.5 mmol) were refluxed in dry degassed acetonitrile (20 mL) for 1 hour, after which the flask was cooled for 30 minutes in an ice bath. The solid material was collected with a Büchner funnel, washed with cold acetonitrile and air dried for 30 minutes (0.9 g). The isothiouronium salt (0.9 g, 2.5 mmol) in DCM (10 mL) was added to a 3-necked flask containing thoroughly degassed water (20 mL). To this was added $Na_2S_2O_5$ (0.6 g, 2.5 mmol), after which the solution was refluxed at 50° C. under argon for 30 minutes and then allowed to cool for a further 10 minutes. An extraction using DCM (3×50 mL), drying over $Na_2SO_4$, followed by removal of solvents under vacuum afforded the title compound as a translucent solid (0.5 g, 37%).

EXAMPLE 17A

The compound of Example 15A (450 mg, 0.99 mmol), the compound of Example 16A (470 mg, 1.53 mmol) and $K_2CO_3$ (260 mg, 1.88 mmol) were refluxed for 1 hour in acetonitrile (20 mL). TLC revealed a spot-to-spot conversion of the Nile red-bromide to a more polar fluorescent product. After purification using silica gel column chromatography (EtOAc:Pet Ether:$NEt_3$=1:1), the title compound was afforded as a purple solid (450 mg, 67% mmol).
Exemplary Compounds

EXAMPLE 1

(3S,4R,5S,6S)-2-(2-((7-chloroquinolin-4-yl)(methyl)amino)ethoxy)-
6-methyltetrahydro-2H-pyran-3,4,5-triol The unpurified compound of Example 12A was dissolved in dry methanol (5 mL), after which NaOMe (30-40% in MeOH, 0.1 mL) was added and the reaction was left to stir under a drying tube for 90 minutes. AcOH (30% in methanol) was added dropwise to lower the pH to 4-6. After quenching the NaOMe, the solvents were removed under vacuum to give the title compound. The identity was confirmed by LCMS (8.91 minutes, m/z 382.7 [M]$^+$).

This compound does not fall within the scope of claim 1 but is provided as a model e.g. for the $^{11}$C-labeled compounds of the invention.

EXAMPLE 2

N-(2-((7-chloroquinolin-4-yl)amino)ethyl)-5-
(dimethylamino)naphthalene-1-sulfonamide The compound of Example 1A (0.5 g, 2.3 mmol) was dissolved in DCM (10 mL) containing $NEt_3$ (1 mL, 6.9 mmol) and the solution was cooled to 0° C. in an ice bath. dansyl chloride (0.6 g, 2.3 mmol) was added as a solid and the reaction was allowed to warm to RT, while stirring under a calcium chloride packed drying tube. Sodium bicarbonate (10 mL) was added and the organic residue extracted into DCM (3×15 mL). The combined organic material was washed with water (10 mL) and then brine (10 mL), dried over $MgSO_4$ and the solvents removed under vacuum. Purification using silica gel column chromatography (MeOH:EtOAc:$NEt_3$=10:90:1) afforded the title compound as a yellow solid (1.0 g, 96%). The identity was confirmed by LCMS (10.94 minutes, m/z 454.7 [M]$^+$).

EXAMPLE 3

7-chloro-N-(2-fluoroethyl)quinolin-
4-amine

A suspension containing the compound of Example 12A (0.83 g, 3.75 mmol) in DCM (15 mL) was prepared. This suspension was added to a 3 necked flask containing Deoxofluor (50% in THF, 1.79 mL, 4.1 mmol) at RT, stirring under argon. Saturated aqueous sodium bicarbonate (50 mL) was added and the residues extracted into DCM (3×30 mL), washed with more sodium bicarbonate until neutral. The organic material was dried over $MgSO_4$, the solvents removed under vacuum and the crude material purified using silica gel column chromatography (MeOH:EtOAc:$NEt_3$=10:

90:1) to afford the title compound as a yellow solid (0.37 g, 44%). The identity was confirmed by LCMS (9.29 minutes, m/z 224.7 [M]+).

This compound does not fall within the scope of claim 1 but is provided as a model for the 18F-labeled compounds of the invention.

EXAMPLE 4

$N^1$-(7-chloroquinolin-4-yl)-$N^2$,$N^2$-dimethylethane-1,2-diamine 4,7-dichloroquinoline (3.0 g, 15.1 mmol) and N,N-dimethylethylenediamine (10.0 g, 113.4 mmol) were heated to 115° C. over night. 6M NaOH (20 mL) was added and the organics extracted into DCM (3×50 mL). After washing with brine (2×100 mL) and drying over MgSO4, the solvents were removed under vacuum, affording the title compound as a light brown solid (3.7 g, 98%). The product shown to be pure by LCMS (2.83 minutes, m/z 249.7 [M]+).

This compound does not fall within the scope of claim 1 but is provided as a model e.g. for the 11C-labeled compounds of the invention.

EXAMPLE 5

9-(diethylamino)-2-(3-(((2R,3S,4R,5S,6S)-3,4,5-trihydroxy-6-methyltetrahydro-2H-pyran-2-yl)thio)propoxy)-5H-benzo[a]phenoxazin-5-one The compound of Example 17A (450 mg, 0.7 mmol) was dissolved in dry methanol (10 mL), to which was added sodium methoxide (30-40% in methanol, 0.1 mL). The reaction was allowed to proceed at RT for 5 hours, after which acetic acid (0.5 mL) was added, the solvents removed under vacuum and the crude residue purified using silica gel column chromatography (EtOAc:methanol=4:1), affording JC106 as a black oil (356 mg, 96% mmol).

Evaluation of the Pharmacological Activity

The pharmacological activity of the compounds of the invention is described below in and in reference to the enclosed drawings.

Figure 1:
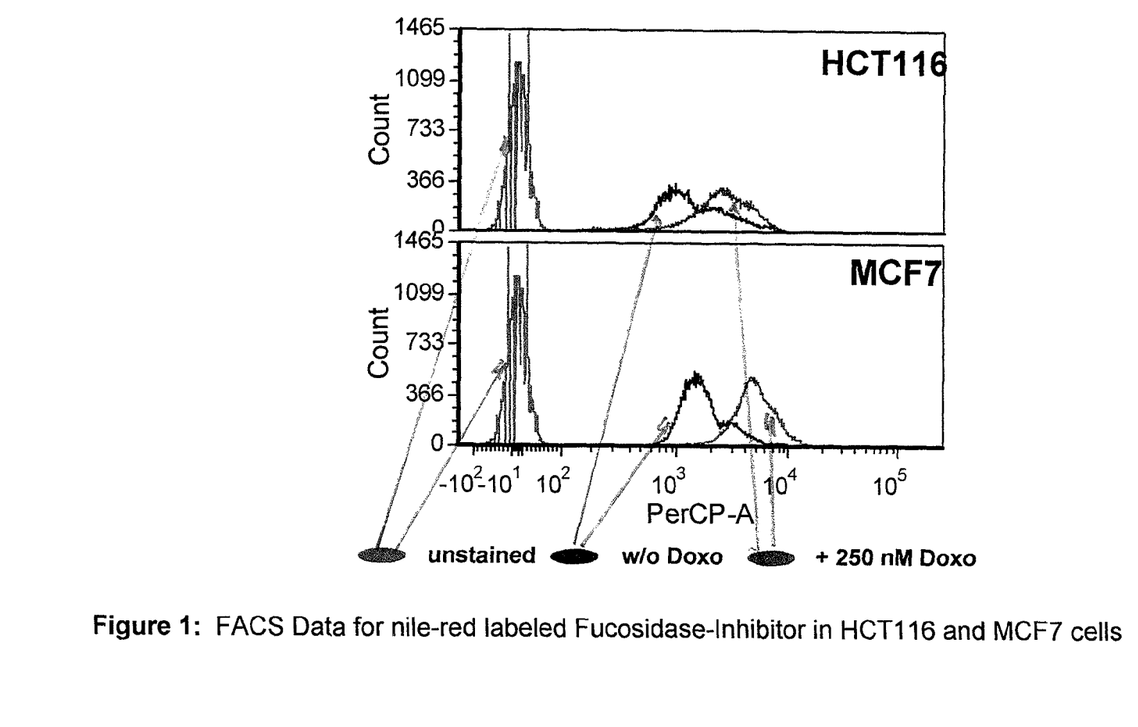
FIG. 1: FACS-analysis data of the compound of Example 5 in HCT116 cells (colorectal carcinoma cell line) and MCF7 cells (breast cancer cell line) with and with out 250 nM Doxorubicin treatment.

To show the capability of the compounds of the invention to mark and visualise senescent cells, HCT116 cells (colorectal carcinoma cell line) and MCF7 cells (breast cancer cell line) were incubated 20 min at 37° C. with 5% $CO_2$ in the presence and absence of Doxorubicin. The cells were then labeled with 40 ng/ml of the compound of Example 5.

MCF7 cells treated with Doxorubicin showed enhanced enrichment of the compound of Example 5 inhibitor indicated by a shift in the direction of PerCP-A. This demonstrates the ability of the compound of Example 5 to bind to and visualize senescent cells.

Figure 2:
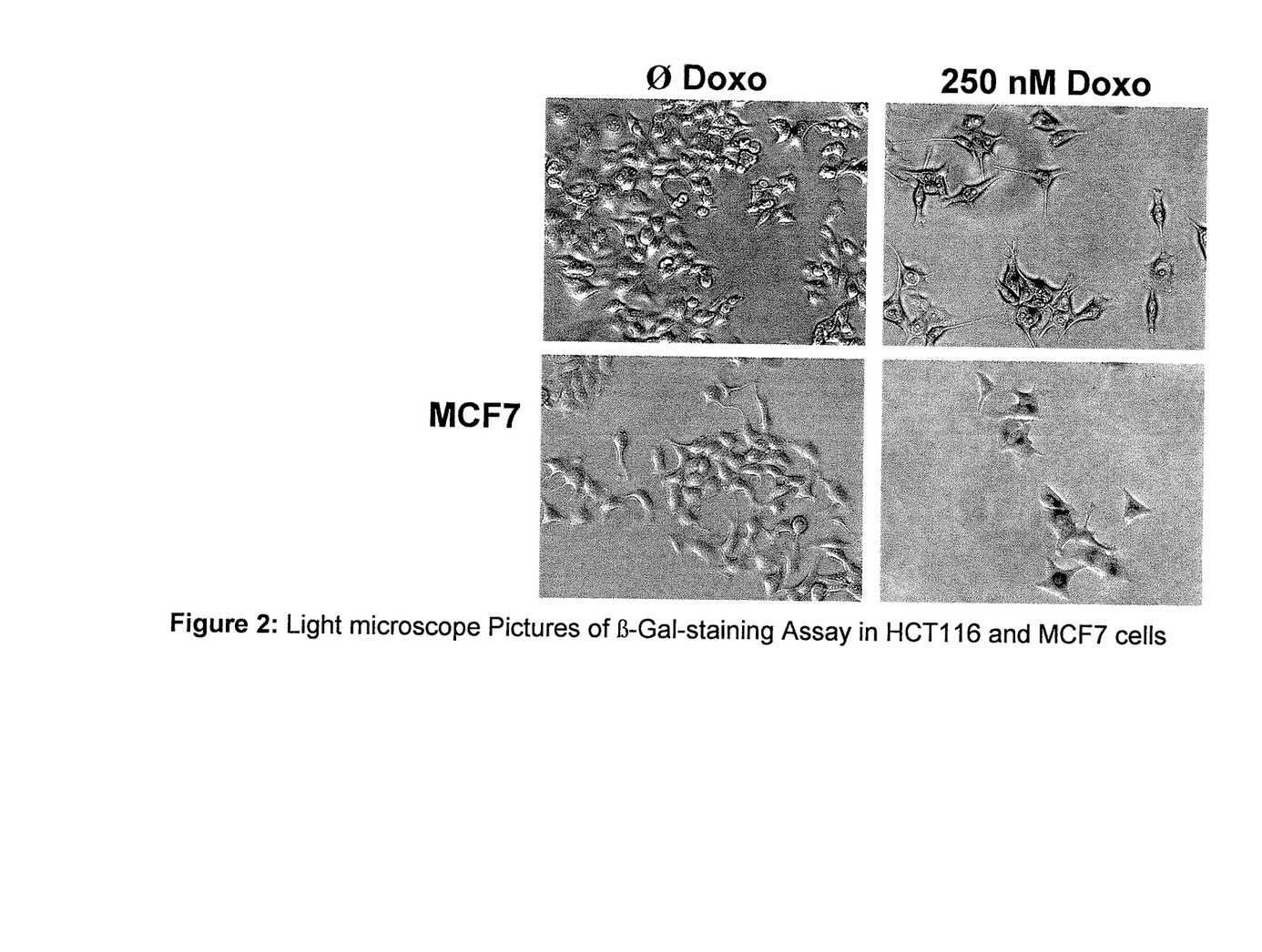
FIG. 2: Light microscope pictures of β-gal-stained HCT116 and MCF7 cells with and with out 250 nM Doxorubicin treatment. Treated cells, mainly MCF7 cells, showed strong β-gal expression.

To stimulate HCT116 (colorectal carcinoma cell line) cells and MCF7 (breast cancer cell line) cells for senescence β-galactosidase staining, the cells were treated with 250nM Doxorubicin for 24 hours. Doxorubicin interacts with DNA by intercalation and inhibits the progression of the enzyme topoisonerase II. FIG. 2 shows representative light microscope pictures of β-gal-stained HCT116 and MCF7 cells with and with out 250 nM Doxorubicin treatment. Doxorubicin treated cells enlarge in senescence and, mainly MCF7 cells, showed strong expression of β-gal (blue), indicating the presence of senescent cells (see FIG. 2).

Figure 3:
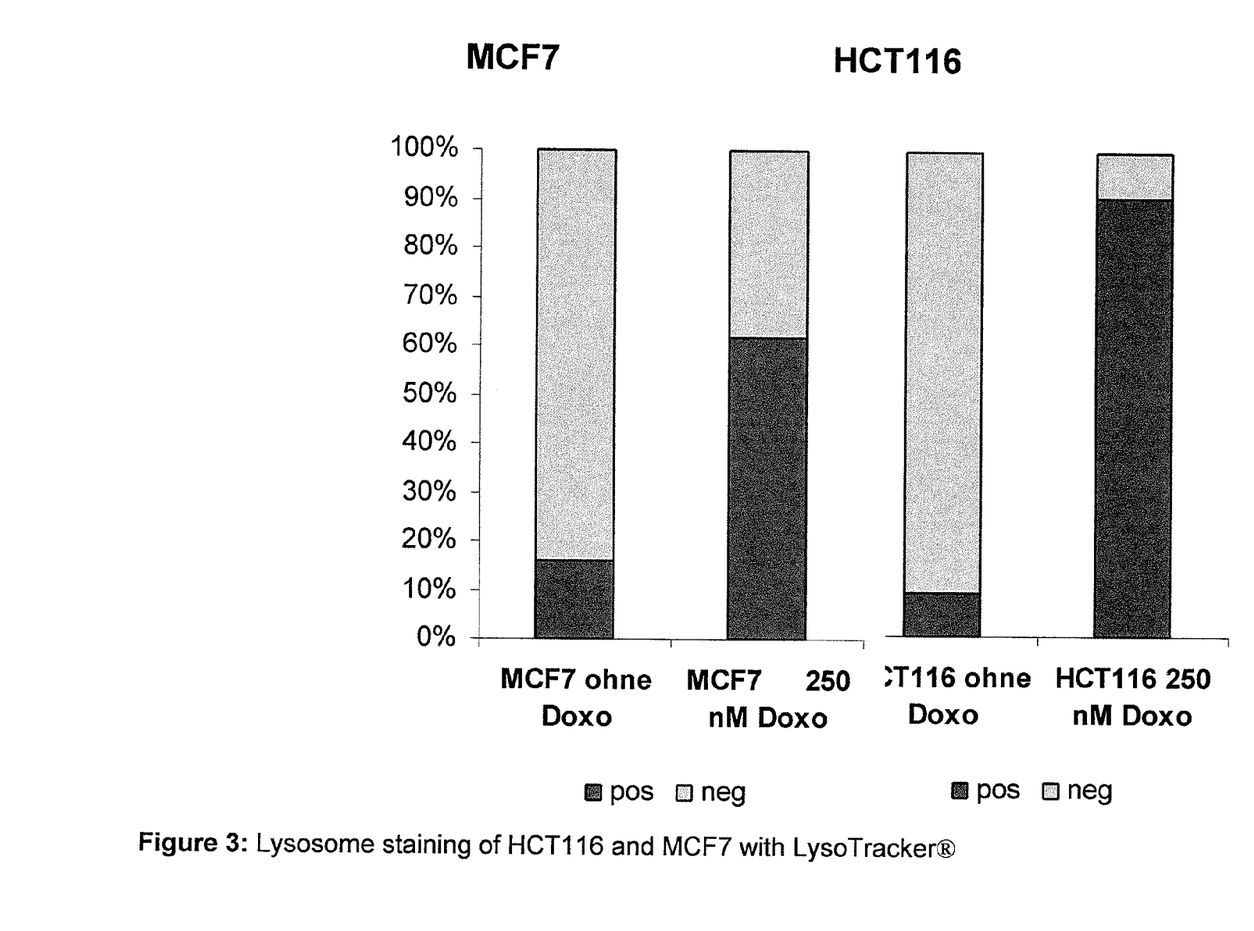
FIG. 3: Graph of staining signals obtained for HCT116 and MCF7 cells stained with LysoTracker® both in the presence and absence of Doxorubicin.

In FIG. 3 a graph is displayed indicating the signal obtained from a lysosome staining of HCT116 (colorectal carcinoma cell line) cells and MCF7 (breast cancer cell line) cells, both in the presence and absence of Doxorubicin. This graph again shows an enhanced positive lysosome staining compared to cells without Doxorubicin treatment (untreated cells), indicating the presence of senescent cells.

To show the capability of the compounds of the invention to mark and visualise senescent cells, HCT116 cells (colorectal carcinoma cell line) and MCF7 cells (breast cancer cell line) were incubated 20 min in 37° C. with 5% $CO_2$. The cells were then labeled with 40 ng/ml of the compound of Example 2. Both HCT116 and MCF7 cells treated with Doxorubicin showed enhanced enrichment of the labeled molecule without the need for permeabilisation (see FIG. 4). This demonstrates the ability of the compound of Example 2 to bind to and visualize senescent cells even in non-permeabilised cells.

Summary

Figure 4:
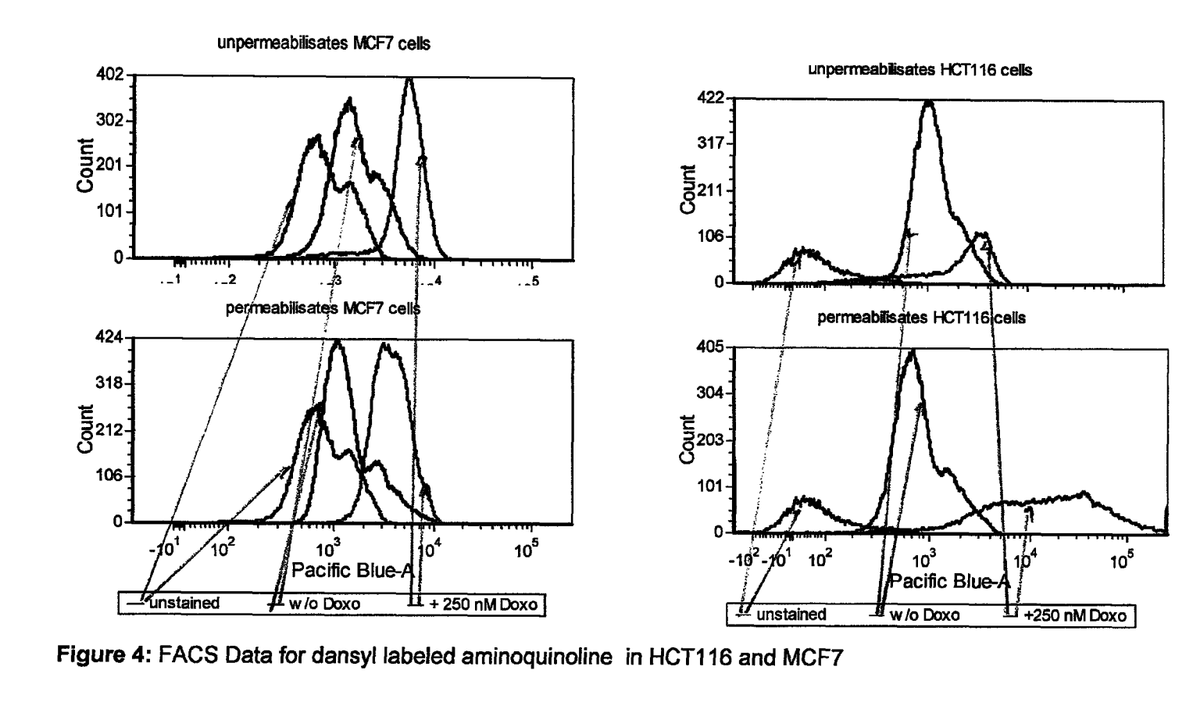

The data displayed in FIG. 2 and FIG. 3 clearly demonstrates the presence of senescent cells in the cell lines treated with Doxorubicin. FIG. 1 and FIG. 4 show clearly that the compounds of the invention accumulate in senescent cells and produce a measurable signal. This shows that the compounds of the invention can serve as markers for senescent cells and can be detected e.g. by optical imaging methods.

What is claimed is:

1. Compound of formula

A-L-M  (I)

in which,

A represents wherein,
* represents the binding site to the residue represented by L,
L represents *Y-(CH$_2$)$_n$-# or wherein,
Y is selected from the group consisting of O, N, S, SO and SO$_2$,
n is an integer from 2 to 6,
* represents the binding site to the residue represented by A, and
# represents the binding site to the residue represented by M, and
M represents a fluorophore, a residue comprising at least one atom selected from the group consisting of $^{76}$Br, $^{75}$Br, $^{18}$F, $^{13}$C and $^{11}$C or a combination thereof, and the salts thereof, the solvates thereof and the solvates of the salts thereof.

2. Compound according to claim 1, wherein n is 2, 3 or 4.

3. Compound according to claim 1, wherein M represents a fluorophore.

4. Compound according to claim 3, wherein the fluorophore is selected from the group consisting of the xanthene derivatives, fluorescein, rhodamine, Oregon green, eosin, and Texas red, the cyanine derivatives, cyanine, indocarbocyanine, oxacarbocyanine, thiacarbocyanine, and merocyanine, the naphthalene derivatives, a dansyl or derivatives thereof, the coumarin derivatives, the oxadiazole derivatives, pyridyloxazole, nitrobenzoxadiazole and benzoxadiazole, the pyrene derivatives, the oxazine derivatives, Nile red, Nile blue and cresyl violet, the acridine derivatives, proflavin, acridine orange and acridine yellow, the arylmethine derivatives, auramine, crystal violet and malachite green, and the tetrapyrrole derivatives, porphin, phthalocyanine and bilirubin.

5. Compound according to claim 1, wherein M is selected from $^{76}$Br, $^{75}$Br, $^{18}$F, wherein,
X is selected from the group consisting of Br, $^{76}$Br, $^{75}$Br, Cl, F and $^{18}$F,
R$_1$ represents hydrogen or (C$_1$-C$_6$)-alkyl,
whereby alkyl is substituted with one to three substituents selected independently from the group consisting of hydroxy, amino, cyano, nitro, halogen, carbonyl, (C$_1$-C$_4$)-alkoxy, mono (C$_1$-C$_4$)-alkylamino and di-(C$_1$-C$_4$)-alkylamino,
whereby R$_1$ represents an optionally substituted (C$_1$-C$_6$)-alkyl comprising at least one $^{76}$Br, $^{75}$Br, $^{18}$F or $^{11}$C if X is not $^{76}$Br, $^{75}$Br or $^{18}$F,
R$_2$ and R$_3$ independently from one another represent hydrogen or (C$_1$-C$_6$)-alkyl,
whereby alkyl is substituted with one to three substituents selected independently form the group consisting of, hydroxy, amino, cyano, nitro, halogen, carbonyl, (C$_1$-C$_4$)-alkoxy, mono (C$_1$-C$_4$)-alkylamino and di-(C$_1$-C$_4$)-alkylamino,
whereby at least one of R$_2$ and R$_3$ represents a (C$_1$-C$_6$)-alkyl comprising at least one $^{11}$C or being substituted with a residue comprising at least one $^{76}$Br, $^{75}$Br, $^{18}$F or $^{11}$C, and
* represents the binding site to the residue represented by L.

6. Medicament comprising a compound according to claim 1 in combination with at least one inert, non-toxic, pharmaceutically suitable excipient.

* * * * *